United States Patent
Maeda et al.

(10) Patent No.: US 9,562,121 B2
(45) Date of Patent: Feb. 7, 2017

(54) OPTICALLY ACTIVE POLY(DIPHENYLACETYLENE) COMPOUND, PREPARATION METHOD THEREFOR, AND USE THEREOF AS OPTICAL ISOMER SEPARATING AGENT

(71) Applicant: NATIONAL UNIVERSITY CORPORATION KANAZAWA UNIVERSITY, Ishikawa (JP)

(72) Inventors: Katsuhiro Maeda, Ishikawa (JP); Shigeyoshi Kanoh, Ishikawa (JP); Tomoyuki Ikai, Ishikawa (JP); Kouhei Shimomura, Aichi (JP); Miyuki Maruta, Ishikawa (JP)

(73) Assignee: NATIONAL UNIVERSITY CORPORATION KANAZAWA UNIVERSITY, Ishikawa (JP)

( * ) Notice: Subject to any disclaimer, the term of this patent is extended or adjusted under 35 U.S.C. 154(b) by 27 days.

(21) Appl. No.: 14/766,853

(22) PCT Filed: Feb. 10, 2014

(86) PCT No.: PCT/JP2014/053001
§ 371 (c)(1),
(2) Date: Aug. 10, 2015

(87) PCT Pub. No.: WO2014/126028
PCT Pub. Date: Aug. 21, 2014

(65) Prior Publication Data
US 2015/0376308 A1    Dec. 31, 2015

(30) Foreign Application Priority Data
Feb. 12, 2013   (JP) .................. 2013-024421

(51) Int. Cl.
| | | |
|---|---|---|
| *C08F 38/00* | (2006.01) | |
| *C08F 138/00* | (2006.01) | |
| *C08F 238/00* | (2006.01) | |
| *C08F 8/00* | (2006.01) | |
| *C08F 8/14* | (2006.01) | |
| *G01N 30/88* | (2006.01) | |
| *B01J 20/29* | (2006.01) | |
| *B01J 20/32* | (2006.01) | |

(52) U.S. Cl.
CPC .............. *C08F 138/00* (2013.01); *B01J 20/29* (2013.01); *B01J 20/3204* (2013.01); *B01J 20/327* (2013.01); *B01J 20/328* (2013.01); *B01J 20/3208* (2013.01); *C08F 8/00* (2013.01); *C08F 8/14* (2013.01); *C08F 38/00* (2013.01); *C08F 238/00* (2013.01); *G01N 30/88* (2013.01); *G01N 2030/8877* (2013.01)

(58) Field of Classification Search
CPC ........ C08F 138/00; C08F 238/00; C08F 38/00
See application file for complete search history.

(56) References Cited

U.S. PATENT DOCUMENTS

| | | |
|---|---|---|
| 2003/0114618 A1 | 6/2003 | Yashima et al. |
| 2008/0220283 A1* | 9/2008 | Sone .................. C08F 8/00 428/689 |

FOREIGN PATENT DOCUMENTS

| | | |
|---|---|---|
| EP | 1 281 723 | 2/2003 |
| JP | 5-271338 | 10/1993 |
| JP | 8-133991 | 5/1996 |
| JP | 2005-239863 | 2/2004 |

OTHER PUBLICATIONS

Fukushima, Macromolecules, 2009, 42, 5453-5460.*
Zhang, ACS Macro Lett., 2012, 1, 75-79.*
Jim, Macromlecules, 2011, 44, 2427-2437.*
Extended European Search Report issued Sep. 19, 2016 in corresponding European patent application No. 14751643.9.
Xiao A. Zhang et al., "Synthesis of Functional Disubstituted Polyacetylenes Bearing Highly Polar Functionalities via Activated Ester Strategy", ACS Macro Letters, vol. 1, No. 1, p. 75-79 (2012).
Cathy K. W. Jim et al., "Helical and Luminescent Disubstituted Polyacetylenes: Synthesis, Helicity, and Light Emission of Poly(diphenylacetylene)s Bearing Chiral Methyl Pendant Groups", Macromolecules, vol. 44, No. 8, p. 2427-2437 (2011).
Toru Katsumata et al., "Polymerization of Diphenylacetylenes with Polar Functional Groups by the Grubbs—Hoveyda Ru Carbene Catalyst", Macromolecular Chemistry and Physics, vol. 207, No. 14, p. 1244-1252 (2006).
Benedict A. San Jose, et al., "Lyotropic Chiral Nematic Liquid Crystalline Aliphatic Conjugated Polymers Based on Disubstituted Polyacetylene Derivatives That Exhibit High Dissymmetry Factors in Circularly Polarized Luminescence", J. Am, Chem. Soc., vol. 134, No. 48, p. 19795-19807 (2012).

(Continued)

*Primary Examiner* — Robert C Boyle
(74) *Attorney, Agent, or Firm* — Wenderoth, Lind & Ponack, L.L.P.

(57) ABSTRACT

The present invention provides an optically active poly (diphenylacetylene) compound represented by the following formula (I):

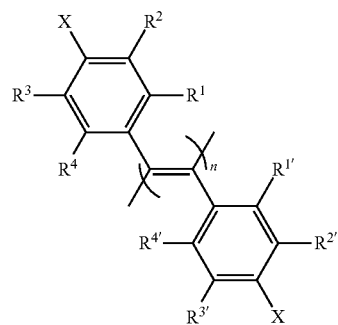

[wherein each symbol is as described in the DESCRIPTION], and a production method thereof, an optical isomer separating agent containing the poly(diphenylacetylene) compound, and a packing material for a chiral column, containing the optical isomer separating agent coated on a carrier. According to the present invention, a practical optical isomer separation agent having a high optical resolution ability for a wide variety of racemic compounds and an optical isomer separation method can be provided.

12 Claims, 2 Drawing Sheets

(56) References Cited

OTHER PUBLICATIONS

Wang Zhang et al., "Disubstituted Polyacetylenes Containing Photopolymerizable Vinyl Groups and Polar Ester Functionality: Polymer Synthesis, Aggregation-Enhanced Emission, and Florescent Pattern Formation", Macromolecules, vol. 40, No. 9, p. 3159-3166 (2007).
Toshiyuki Fukushima et al., "Synthesis and Chirality Control of Optically Active Poly(diphenylacetylene) Derivatives", Macromolecules, vol. 42, No. 15, p. 5453-5460 (2009).
Toshiki Aoki et al., "Synthesis and Properties of Polymers from Disubstituted Acetylenes with Chiral Pinanyl Groups", Macromolecules, vol. 32, No. 1, p. 79-85 (1999).
Masahiro Teraguchi et al., "Poly(diphenylacetylene) Membranes with High Gas Permeability and Remarkable Chiral Memory", Marcomolecules, vol. 35, No. 4, p. 1149-1151 (2002).
Masahiro Teraguchi et al., "Enantioselective Permeation through Membranes of Chiral Helical Polymers Prepared by Depinanylsilylation of Poly(diphenylacetylene) with a High Content of the Pinanylsilyl Group", Macromolecules, vol. 36, No. 26, p. 9694-9697 (2003).
Daehoon Lee et al., "Solvent-to-Polymer Chirality Transfer in Intramolecular Stack Structure", Macromolecules, vol. 45, No. 13, p. 5379-5386 (2012).
Daehoon Lee et al., "Optically active, lyotropic liquid crystalline poly(diphenylacetylene) derivative: hierarchical chiral ordering from isotropic solution to anisotropic solid films", Chem. Commun., vol. 48, p. 9275-9277 (2012).
Hashimoto, K. et al., "Chirality Induction in an Optical Inactive Water-soluble Poly(diphenylacetylene) Derivative", Polymer Preprints, Japan, Sep. 5, 2012, vol. 61, No. 2, p. 2561.
International Search Report issued Mar. 25, 2014 in International Application No. PCT/JP2014/053001. (English Translation).
International Preliminary Report on Patentability issued Jan. 5, 2015 in International Patent Application No. PCT/JP2014/053001. (English Translation).

* cited by examiner

OPTICALLY ACTIVE POLY(DIPHENYLACETYLENE) COMPOUND, PREPARATION METHOD THEREFOR, AND USE THEREOF AS OPTICAL ISOMER SEPARATING AGENT

TECHNICAL FIELD

The present invention relates to an optical isomer separating agent used for separating an optical isomer by a chromatography method, particularly liquid chromatography, and a packing material supporting same, and particularly relates to an optically active poly(diphenylacetylene) compound useful as a separating agent for a mixture of optical isomers of a wide variety of chiral compounds and a production method thereof.

BACKGROUND ART

Organic compounds include many optical isomers having completely the same physical, chemical properties, for example, properties such as boiling point, melting point, solubility but showing different physiological activities. In the technical field of medicaments, differences in the pharmacological activity depending on the easiness of binding with a particular receptor in the body have been studied much, and it is widely known that remarkable differences in drug efficacy and toxicity are often found between optical isomers. Guideline for drug production by the Ministry of Health, Labour and Welfare also describes that it is desirable to study absorption, distribution, metabolism and excretion kinetics of each isomer when a racemate is used as a drug.

As described above, since optical isomers show completely the same physical and chemical properties, they cannot be analyzed by general separation means. Thus, the study of techniques for easily and precisely analyzing optical isomers of a wide variety of organic compounds has been extensively conducted. Of such techniques, particularly, the optical resolution method by high performance liquid chromatography (hereinafter sometimes to be also referred to as HPLC) separates optical isomers by using a substance having an ability to separate optical isomers, i.e., an optical isomer separating agent, per se, or a chiral stationary phase supporting an optical isomer separating agent on a suitable carrier by a chemical bond or coating. For example, a packing material comprising an optically active crown ether compound, which is a low-molecular-weight compound, coated on a carrier (patent document 1), a packing material comprising an optically active triphenylmethyl methacrylate polymer, which is a synthetic polymer, coated on a carrier (patent document 2), a packing material comprising cellulose triacetate, which is a polysaccharide derivative, coated on a carrier (patent document 3), a packing material comprising cellulose benzoate coated on a carrier (patent document 4), a packing material comprising cellulose phenylcarbamate coated on a carrier (patent document 5), a packing material comprising a cellulose or amylose derivative (non-patent document 1), ovomucoid which is a protein (patent document 6) and the like have been developed and, in view of their high optical resolution ability, commercialized and widely used.

DOCUMENT LIST

Patent Documents patent document 1: JP-A-S62-210053
patent document 2: JP-A-S57-150432
patent document 3: JP-A-S60-82858
patent document 4: JP-A-S60-40952
patent document 5: JP-A-S60-108751
patent document 6: JP-A-S63-307829

Non-Patent Document non-patent document 1: Okamoto, Y., Kawashima, M. and Hatada, K. J. Am. Chem. Soc., 1984, 106, 5357.

SUMMARY OF THE INVENTION

Problems to be Solved by the Invention

However, optical isomer separating agents are generally very expensive. While all optical isomer separating agents are superior in the separating ability of particular object compounds (racemates), the range of the optically resolvable compound is extremely limited. Therefore, to expand the range of optically resolvable object compound, the development of a new optical isomer separating agent having a chemical structure different from those of the existing optical isomer separating agents and thereby showing different optical resolution property has been desired.

Means of Solving the Problems

The present inventors have conducted intensive studies under the circumstances and found for the first time that an optically active poly(diphenylacetylene) compound represented by the following formula (I):

[wherein
$R^1$, $R^{1'}$, $R^2$, $R^{2'}$, $R^3$, $R^{3'}$, $R^4$ and $R^{4'}$ are each independently a hydrogen atom, a halogen atom, an optionally substituted alkyl group, an optionally substituted cycloalkyl group, an optionally substituted alkoxy group, an optionally substituted alkylthio group, a tri-substituted silyl group, a tri-substituted siloxy group or an optionally substituted acyloxy group;
X is a carboxy group amidated or esterified by condensation with an optically active chiral compound; and
n is an integer of not less than 10]
(hereinafter sometimes to be also referred to as "compound (I)") or a salt thereof, or a solvate thereof, and a poly(diphenylacetylene) compound which is compound (I) having a one-handed helical structure in the main chain (hereinafter sometimes to be also simply referred to as "compound (I-h)") or a salt thereof, or a solvate thereof are useful as a separating agent for an optical isomer mixture of a wide variety of chiral compounds, which resulted in the completion of the present invention.

Therefore, the present invention provides the following.

[1] A poly(diphenylacetylene) compound represented by the formula (I):

[wherein
$R^1$, $R^{1'}$, $R^2$, $R^{2'}$, $R^3$, $R^{3'}$, $R^4$ and $R^{4'}$ are each independently a hydrogen atom, a halogen atom, an optionally substituted alkyl group, an optionally substituted cycloalkyl group, an optionally substituted alkoxy group, an optionally substituted alkylthio group, a tri-substituted silyl group, a tri-substituted siloxy group or an optionally substituted acyloxy group;
X is a carboxy group amidated or esterified by condensation with an optically active chiral compound; and
n is an integer of not less than 10],
or a salt thereof, or a solvate thereof.

[2] The compound of the above-mentioned [1], which has a one-handed helical structure, or a salt thereof, or a solvate thereof.

[3] The compound of the above-mentioned [1] or [2], wherein each of $R^1$ and $R^{1'}$, $R^2$ and $R^{2'}$, $R^3$ and $R^{3'}$, and $R^4$ and $R^{4'}$ are the same group, or a salt thereof, or a solvate thereof.

[4] The compound of any of the above-mentioned [1]-[3], wherein X is a carboxy group amidated or esterified by condensation with an optically active form of a chiral compound selected from the group consisting of 1-phenylethylamine, 1-cyclohexylethylamine, 1-(1-naphthyl)ethylamine, 1-(2-naphthyl)ethylamine, sec-butylamine, 1-phenyl-2-(p-tolyl)ethylamine, 1-(p-tolyl)ethylamine, 1-(4-methoxyphenyl)ethylamine, β-methylphenethylamine, 2-amino-1-butanol, 2-amino-1,2-diphenylethanol, 1-amino-2-indanol, 2-amino-1-phenyl-1,3-propanediol, 2-amino-1-propanol, leucinol, phenylalaninol, 2-phenylglycinol, valinol, norephedrine, methioninol, 1-benzyl-3-aminopyrrolidine, 2-(methoxymethyl)pyrrolidine, 1-methyl-2-(1-piperidinomethyl)pyrrolidine, 1-(2-pyrrolidinomethyl)pyrrolidine, 1-phenylethylalcohol, 1-phenyl-2-propanol, 1,2,3,4-tetrahydro-1-naphthol, 1-acetyl-3-pyrrolidinol, 1-benzyl-3-pyrrolidinol, 2-butanol, α-hydroxy-γ-butyrolactone, 3-hydroxytetrahydrofuran, 1-methyl-3-pyrrolidinol, 2-octanol, 2-pentanol, 1-(2-naphthyl)ethanol, menthol, borneol, quinidine, quinine, quincorine, quincoridine, cinchonidine, cinchonine and an amino acid having a protected carboxy group, or a salt thereof, or a solvate thereof.

[5] The compound of the above-mentioned [1] or [2], wherein $R^1$, $R^{1'}$, $R^2$, $R^{2'}$, $R^3$, $R^{3'}$, $R^4$ and $R^{4'}$ are each independently a hydrogen atom, a halogen atom, a $C_{1-6}$ alkyl group optionally substituted by halogen atom(s), a $C_{1-6}$ alkoxy group optionally substituted by halogen atom(s), a tri $C_{1-6}$ alkylsilyl group or a tri $C_{1-6}$ alkylsiloxy group, and each of $R^1$ and $R^{1'}$, $R^2$ and $R^{2'}$, $R^3$ and $R^{3'}$, and $R^4$ and $R^{4'}$ are the same group;
X is a carboxy group amidated by condensation with an optically active form of a compound selected from the group consisting of 1-phenylethylamine, 1-cyclohexylethylamine, 1-(1-naphthyl)ethylamine, 1-(2-naphthyl)ethylamine, sec-butylamine, 1-phenyl-2-(p-tolyl)ethylamine, 1-(p-tolyl)ethylamine, 1-(4-methoxyphenyl)ethylamine, β-methylphenethylamine, 2-amino-1-butanol, 2-amino-1,2-diphenylethanol, 1-amino-2-indanol, 2-amino-1-phenyl-1,3-propanediol, 2-amino-1-propanol, leucinol, phenylalaninol, 2-phenylglycinol, valinol, norephedrine, methioninol, 1-benzyl-3-aminopyrrolidine, 2-(methoxymethyl)pyrrolidine, 1-(2-pyrrolidinomethyl)pyrrolidine and an amino acid having a protected carboxy group; and
n is an integer of not less than 10 and not more than 10000, or a salt thereof, or a solvate thereof.

[6] The compound of the above-mentioned [1] or [2], wherein $R^1$, $R^{1'}$, $R^2$, $R^{2'}$, $R^3$, $R^{3'}$, $R^4$ and $R^{4'}$ are each independently a hydrogen atom or a halogen atom, and each of $R^1$ and $R^{1'}$, $R^2$ and $R^{2'}$, $R^3$ and $R^{3'}$, and $R^4$ and $R^{4'}$ is the same group;
X is a carboxy group amidated by condensation with (S)-(−)-1-phenylethylamine or (R)-(+)-1-phenylethylamine; and
n is an integer of not less than 100 and not more than 10000, or a salt thereof, or a solvate thereof.

[7] An optical isomer separating agent comprising the poly(diphenylacetylene) compound of any of the above-mentioned [1]-[6].

[8] A packing material comprising the optical isomer separating agent of the above-mentioned [7] supported on a carrier.

[9] The packing material of the above-mentioned [8], wherein the carrier is silica gel.

[10] A chiral column prepared by packing with the packing material of the above-mentioned [8] or [9].

[11] The chiral column of the above-mentioned [10], which is for use for the purity measurement or separation of a mixture of optical isomers.

[12] A production method of the compound of the above-mentioned [2], or a salt thereof, or a solvate thereof, comprising a step of amidating or esterifying the carboxy group of the poly(diphenylacetylene) compound represented by the formula (II):

[wherein
$R^1$, $R^{1'}$, $R^2$, $R^{2'}$, $R^3$, $R^{3'}$, $R^4$ and $R^{4'}$ are each independently a hydrogen atom, a halogen atom, an optionally substituted alkyl group, an optionally substituted cycloalkyl group, an optionally substituted alkoxy group, an optionally substituted alkylthio group, a tri-substituted silyl group, a tri-substituted siloxy group or an optionally substituted acyloxy group; and n is an integer of not less than 10], by condensing with an optically active chiral compound, and a step of heat treating the aforementioned amidated or esterified compound.

[13] The method of the above-mentioned [12], wherein the heat treatment is performed at about 90° C.

[14] The method of the above-mentioned [12] or [13], wherein the optically active chiral compound is an optically active form of a compound selected from the group consisting of 1-phenylethylamine, 1-cyclohexylethylamine, 1-(1-naphthyl)ethylamine, 1-(2-naphthyl)ethylamine, sec-butylamine, 1-phenyl-2-(p-tolyl)ethylamine, 1-(p-tolyl)ethylamine, 1-(4-methoxyphenyl)ethylamine, β-methylphenethylamine, 2-amino-1-butanol, 2-amino-1, 2-diphenylethanol, 1-amino-2-indanol, 2-amino-1-phenyl-1,3-propanediol, 2-amino-1-propanol, leucinol, phenylalaninol, 2-phenylglycinol, valinol, norephedrine, methioninol, 1-benzyl-3-aminopyrrolidine, 2-(methoxymethyl)pyrrolidine, 1-methyl-2-(1-piperidinomethyl)pyrrolidine, 1-(2-pyrrolidinomethyl)pyrrolidine, 1-phenylethylalcohol, 1-phenyl-2-propanol, 1,2,3,4-tetrahydro-1-naphthol, 1-acetyl-3-pyrrolidinol, 1-benzyl-3-pyrrolidinol, 2-butanol, α-hydroxy-γ-butyrolactone, 3-hydroxytetrahydrofuran, 1-methyl-3-pyrrolidinol, 2-octanol, 2-pentanol, 1-(2-naphthyl)ethanol, menthol, borneol, quinidine, quinine, quincorine, quincoridine, cinchonidine, cinchonine and an amino acid having a protected carboxy group.

[15] The method of any of the above-mentioned [12]-[14], wherein the amidation or esterification step is an amidation step.

[16] The method of the above-mentioned [15], wherein the optically active chiral compound is (S)-(−)-1-phenylethylamine or (R)-(+)-1-phenylethylamine.

Effect of the Invention

Compound (I) and compound (I-h) of the present invention have superior optical resolution ability for a wide range of chiral compounds. According to the present invention, compound (I) and compound (I-h) can be synthesized conveniently. Since a commercially available compound can be widely used as an optically active chiral compound to be used for the production of compound (I), it is advantageous in that the kind thereof and absolute configuration thereof can be easily selected and optimized according to the kind of separation target compound and elution order.

BRIEF DESCRIPTION OF THE DRAWINGS

FIG. 1 (a) shows CD and UV spectra of compound (Ia) measured in dimethyl sulfoxide/N,N-dimethylformamide (2:1, v/v), and (b) shows CD and UV spectra of compound (Ia-h) measured in dimethyl sulfoxide/N,N-dimethylformamide (2:1, v/v).

DESCRIPTION OF EMBODIMENTS

The detail of the present invention is explained in the following.

(Definition)

In the present specification, the "halogen atom" means a fluorine atom, a chlorine atom, a bromine atom or an iodine atom.

In the present specification, the "alkyl (group)" means a straight chain or branched chain alkyl group having one or more carbon atoms. When the range of the carbon atom number is not particularly limited, it is preferably a $C_{1-20}$ alkyl group, more preferably a $C_{1-12}$ alkyl group, particularly preferably a $C_{1-6}$ alkyl group.

In the present specification, the "$C_{1-20}$ alkyl (group)" means a straight chain or branched chain alkyl group having 1-20 carbon atoms, and examples thereof include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl, undecyl, dodecyl, tridecyl, eicosyl and the like.

In the present specification, the "$C_{1-12}$ alkyl (group)" means a straight chain or branched chain alkyl group having 1-12 carbon atoms, and examples thereof include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl, undecyl, dodecyl and the like.

In the present specification, the "$C_{1-6}$ alkyl (group)" means a straight chain or branched chain alkyl group having 1-6 carbon atoms, and examples thereof include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl and the like.

In the present specification, the "cycloalkyl (group)" means a cyclic alkyl group. When the range of the carbon atom number is not particularly limited, it is preferably a $C_{3-8}$ cycloalkyl group.

In the present specification, the "$C_{3-8}$ cycloalkyl (group)" means a cyclic alkyl group having 3-8 carbon atoms, and examples thereof include cyclopropyl, cyclobutyl, cyclopentyl, cyclohexyl, cycloheptyl, cyclooctyl and the like. Of these, a $C_{3-6}$ cycloalkyl group is preferable.

In the present specification, the "alkoxy (group)" means a group wherein a straight chain or branched chain alkyl group is bonded to an oxygen atom, and the range of the carbon atom number is not particularly limited. Preferred is a $C_{1-6}$ alkoxy group.

In the present specification, the "$C_{1-6}$ alkoxy (group)" means a straight chain or branched chain alkoxy group having 1-6 carbon atoms, and examples thereof include methoxy, ethoxy, propoxy, isopropoxy, butoxy, isobutoxy, sec-butoxy, tert-butoxy, pentyloxy, isopentyloxy, neopentyloxy, hexyloxy and the like. Of these, a $C_{1-4}$ alkoxy group is preferable.

In the present specification, the "alkylthio (group)" means a group wherein a straight chain or branched chain alkyl group is bonded to a sulfur atom, and the range of the carbon atom number is not particularly limited. Preferred is a $C_{1-6}$ alkylthio group.

In the present specification, the "$C_{1-6}$ alkylthio (group)" means a straight chain or branched chain alkylthio group having 1-6 carbon atoms, and examples thereof include methylthio, ethylthio, propylthio, isopropylthio, butylthio, isobutylthio, sec-butylthio, tert-butylthio, pentylthio, isopentylthio, neopentylthio, hexylthio and the like. Of these, a $C_{1-4}$ alkylthio group is preferable.

In the present specification, the "acyl (group)" means alkanoyl or aroyl, and the range of the carbon atom number is not particularly limited. Preferred is a $C_{1-7}$ alkanoyl group or $C_{7-11}$ aroyl.

In the present specification, the "$C_{1-7}$ alkanoyl (group)" is a straight chain or branched chain formyl or alkylcarbonyl having 1-7 carbon atoms, and examples thereof include formyl, acetyl, propionyl, butyryl, isobutyryl, pentanoyl, hexanoyl, heptanoyl and the like.

In the present specification, the "$C_{7-11}$ aroyl (group)" is arylcarbonyl having 7-11 carbon atoms, and examples thereof include benzoyl and the like.

In the present specification, the "acyloxy (group)" means a group wherein an alkanoyl group or an aroyl group is bonded to an oxygen atom, and the range of the carbon atom number is not particularly limited. Preferred is a $C_{1-7}$ alkanoyloxy group or a $C_{7-11}$ aroyloxy group.

In the present specification, examples of the "$C_{1-7}$ alkanoyloxy (group)" include formyloxy, acetoxy, ethylcarbonyloxy, propylcarbonyloxy, isopropylcarbonyloxy, butylcarbonyloxy, isobutylcarbonyloxy, sec-butylcarbonyloxy, tert-butylcarbonyloxy, pentylcarbonyloxy, isopentylcarbonyloxy, neopentylcarbonyloxy, hexylcarbonyloxy and the like.

In the present specification, examples of the "$C_{7-11}$ aroyloxy (group)" include benzoyloxy, 1-naphthoyloxy, 2-naphthoyloxy and the like.

In the present specification, the "aryl (group)" means an aromatic monocyclic or aromatic polycyclic (fused) hydrocarbon group, and specific examples thereof include $C_{6-14}$ aryl groups such as phenyl, 1-naphthyl, 2-naphthyl, biphenylyl, 2-anthryl and the like. Of these, a $C_{6-10}$ aryl group is preferable.

In the present specification, the "$C_{6-10}$ aryl (group)" is, for example, phenyl, 1-naphthyl or 2-naphthyl, and phenyl is particularly preferable.

In the present specification, the "aralkyl (group)" means a group wherein an alkyl group is substituted by an aryl group, and the range of the carbon atom number is not particularly limited. Preferred is $C_{7-14}$ aralkyl.

In the present specification, the "$C_{7-14}$ aralkyl (group)" means a group wherein the "$C_{1-4}$ alkyl group" is substituted by the "$C_{6-10}$ aryl group", and examples thereof include benzyl, 1-phenylethyl, 2-phenylethyl, (naphthyl-1-yl)methyl, (naphthyl-2-yl)methyl, 1-(naphthyl-1-yl)ethyl, 1-(naphthyl-2-yl)ethyl, 2-(naphthyl-1-yl)ethyl, 2-(naphthyl-2-yl)ethyl, biphenylylmethyl and the like.

In the present specification, the "tri-substituted silyl (group)" means a silyl group substituted by the same or different three substituents (e.g., $C_{1-6}$ alkyl group, $C_{6-10}$ aryl group etc.), and preferable examples of the group include trialkylsilyl groups such as trimethylsilyl group, triethylsilyl group, triisopropylsilyl group, tert-butyldimethylsilyl group and the like (preferably, tri $C_{1-6}$ alkylsilyl group), tert-butyldiphenylsilyl group, triphenylsilyl group and the like.

In the present specification, the "tri-substituted siloxy (group)" means a group wherein a tri-substituted silyl group is bonded to an oxygen atom. As the group, trialkylsiloxy group such as trimethylsiloxy group, triethylsiloxy group, triisopropylsiloxy group, tert-butyldimethylsiloxy group and the like (preferably, tri $C_{1-6}$ alkylsiloxy group) is preferable.

In the present specification, "optionally substituted" means optionally having one or more substituents, and examples of the "substituent" include (1) a halogen atom, (2) $C_{1-6}$ alkyl, (3) $C_{3-8}$ cycloalkyl, (4) $C_{1-6}$ alkoxy, (5) $C_{6-10}$ aryl, (6) $C_{7-14}$ aralkyl, (7) $C_{1-6}$ alkylthio, (8) tri $C_{1-6}$ alkylsilyl group and the like. Of these, a halogen atom, $C_{1-6}$ alkyl, $C_{1-6}$ alkoxy, trimethylsilyl, triethylsilyl, triisopropylsilyl, tert-butyldimethylsilyl and the like are preferable, and a halogen atom is more preferable. When plural substituents are present, the respective substituents may be the same or different.

In the present specification, the "one-handed helical structure" may be a right-handed or left-handed lopsided helical structure, and it is preferably a completely right-handed or left-handed helical structure. A compound having a "one-handed helical structure" shows optical activity due to the lopsided helical structure alone, even when it does not have an optically active functional group in a molecule.

In the present specification, "optically active" means the property to rotate plane polarized light, that is, having an optical rotatory power. It is preferably an optically pure state.

In the present specification, the "optically active chiral compound" is a low-molecular-weight compound having the property to rotate plane-polarized light, that is, having an optical rotatory power, and an organic compound having a molecular weight of 1000 or below, and is not particularly limited. Preferably, it is an optically pure compound having one asymmetric carbon atom, and examples thereof include optically active forms of chiral compounds such as 1-phenylethylamine, 1-cyclohexylethylamine, 1-(1-naphthyl)ethylamine, 1-(2-naphthyl)ethylamine, sec-butylamine, 1-phenyl-2-(p-tolyl)ethylamine, 1-(p-tolyl)ethylamine, 1-(4-methoxyphenyl)ethylamine, β-methylphenethylamine, 2-amino-1-butanol, 2-amino-1,2-diphenylethanol, 1-amino-2-indanol, 2-amino-1-phenyl-1,3-propanediol, 2-amino-1-propanol, leucinol, phenylalaninol, 2-phenylglycinol, valinol, norephedrine, methioninol, 1-benzyl-3-aminopyrrolidine, 2-(methoxymethyl)pyrrolidine, 1-methyl-2-(1-piperidinomethyl)pyrrolidine, 1-(2-pyrrolidinomethyl)pyrrolidine, 1-phenylethylalcohol, 1-phenyl-2-propanol, 1,2,3,4-tetrahydro-1-naphthol, 1-acetyl-3-pyrrolidinol, 1-benzyl-3-pyrrolidinol, 2-butanol, α-hydroxy-γ-butyrolactone, 3-hydroxytetrahydrofuran, 1-methyl-3-pyrrolidinol, 2-octanol, 2-pentanol, 1-(2-naphthyl)ethanol, menthol, borneol, quinidine, quinine, quincorine, quincoridine, cinchonidine, cinchonine, an amino acid having a protected carboxy group and the like, whose optically pure, both enantiomers are available as commercially available products. Of these, (R)-(+)-1-phenylethylamine or (S)-(−)-1-phenylethylamine is particularly preferable. As the optically active chiral compound, an optically pure compound is preferably used. It is also possible to induce a lopsided helical structure in the poly(diphenylacetylene) main chain by using compound (I) amidated or esterified using a compound having low optical purity. Therefore, the "optically active chiral compound" encompasses not only an optically pure compound, but also a compound having a low optical purity. The low-molecular-weight compound may be liquid or solid, preferably liquid.

In the present specification, "ee" is an abbreviation of enantiomeric excess, and shows optical purity of a chiral compound. The "ee" is calculated by subtracting a smaller amount of substance of enantiomer from a larger amount of substance of enantiomer, dividing the value by the whole amount of substance and multiplying the value by 100, and is shown by "% ee".

In the present specification, "optically pure" means a state of optical purity of not less than 99% ee.

In the present specification, the "enantiomer" means an optical antipode having different steric configurations of all asymmetric carbon atoms in an optically active low-molecular-weight compound, which constitutes a pair of optical isomers in the right hand-left hand relationship to the optically active low-molecular-weight compound. Specifically, for example, when the optically active low-molecular-weight compound is (R)-(−)-2-phenylglycinol, the enantiomer is (S)-(+)-2-phenylglycinol.

In the present specification, "chiral compound" means a compound having central chirality, axial chirality or planar chirality and, for example, a compound having central chirality (asymmetric center, i.e., asymmetric carbon atom) can be mentioned.

In the present specification, the "racemate" means a compound that does not show optical rotation due to the presence of equal amounts of two kinds of enantiomers of a chiral compound.

In the present specification, the "optical isomer separating agent" only needs to be a substance having an ability to separate a mixture of optical isomers of a chiral compound, and is not particularly limited.

Examples of a method of optical resolution of an optically active compound by using the optical isomer separating agent of the present invention include, but are not particularly limited, chromatography methods such as gas chromatography, liquid chromatography, supercritical chromatography, thin layer chromatography, capillary electrophoresis and the like, optical isomer separation by membrane separation and the like.

When the optical isomer separating agent of the present invention is used, for example, as a stationary phase of a column packing material for high performance liquid chromatography, the eluent is not particularly limited as long as it is not a liquid that dissolves or reacts with the separating agent of the present invention, and the separating agent is applicable to both a normal-phase using hexane-2-propanol and the like, and a reverse-phase using alcohol-water and the like.

In the present invention, compound (I) or compound (I-h) per se can also be used as an optical isomer separating agent. However, it is preferably supported on some carrier for the purpose of improving the pressure resistance of the separating agent, preventing swelling and contraction due to solvent substitution, improving the number of theoretical plates and the like.

Examples of the carrier to be used in the present invention include porous organic carrier and porous inorganic carrier, with preference given to porous inorganic carrier. Suitable as a porous organic carrier is a polymer substance composed of polystyrene, polyacrylamide, polyacrylate and the like, and suitable as a porous inorganic carrier are silica gel, alumina, magnesia, glass, kaolin, titanium oxide, silicate, hydroxyapatite and the like. Particularly preferred carrier is silica gel.

A method of supporting the compound (I) or compound (I-h) of the present invention on a carrier is not particularly limited and may be a physical method or a chemical method. Examples of the physical method include a method of contacting compound (I) or compound (I-h) with a porous inorganic carrier or porous organic carrier. Examples of the chemical method include a method of imparting, during the production of compound (I) or compound (I-h), a functional group to a terminus of the polymer thereof, and chemically binding the functional group to a functional group on the surface of a porous inorganic carrier or a porous organic carrier.

The amount of the compound (I) or compound (I-h) of the present invention to be supported varies depending on the kind and property of the carrier to be used and is not particularly limited. It is generally within the range of 1-1000 wt % relative to the weight of the carrier.

The packing material of the present invention is generally used for optical isomer separation by the chromatography method such as gas chromatography, liquid chromatography, supercritical chromatography, thin layer chromatography, capillary electrophoresis and the like, or membrane separation, and particularly preferably applied to the liquid chromatography method.

Furthermore, the packing material of the present invention is preferably used for an analytical chiral column of high performance liquid chromatography mainly aiming at optical purity measurement, a preparative chiral column of single column system liquid chromatography aiming at obtaining several mg—several kg of an optically active form, a preparative chiral column of continuous liquid chromatography represented by a simulated moving bed system and the like.

The optical isomer separating agent of the present invention is utilizable not only for the above-mentioned packing material for liquid chromatography, but also as a shift reagent for nuclear magnetic resonance spectrum (NMR) and the like.

A mixture of optical isomers that can be separated by the optical isomer separating agent of the present invention, or a chiral column using a packing material supporting the optical isomer separating agent as a chiral stationary phase is not particularly limited, and can be preferably used for the separation of optical isomers of a wide variety of low-molecular-weight compounds having a molecular weight of not more than 500. Examples of the low-molecular-weight compound include, but are not particularly limited to, substituted cyclopropanes, substituted cyclobutanes, 2-phenylcyclohexanone, optionally substituted binaphthol, alcohols, metal acetylacetonate complex (e.g., cobalt etc.) and the like.

(Compound (I) and Compound (I-h) of the Present Invention)

Compound (I) of the present invention is a poly(diphenylacetylene) compound represented by the following formula (I):

(I)

[wherein
$R^1$, $R^{1'}$, $R^2$, $R^{2'}$, $R^3$, $R^{3'}$, $R^4$ and $R^{4'}$ are each independently a hydrogen atom, a halogen atom, an optionally substituted alkyl group, an optionally substituted cycloalkyl group, an optionally substituted alkoxy group, an optionally substituted alkylthio group, a tri-substituted silyl group, a tri-substituted siloxy group or an optionally substituted acyloxy group;

X is a carboxy group amidated or esterified by condensation with an optically active chiral compound; and n is an integer of not less than 10], and compound (I-h) of the present invention is compound (I) having a one-handed helical structure in the polymer main chain thereof.

Examples of the salt of the compound (I) (or the salt of the compound (I-h)) of the present invention include a salt with an inorganic acid, a salt with an organic acid, a salt with an inorganic base, a salt with an organic base, a salt with an amino acid and the like.

Examples of the salt with an inorganic acid include salts with hydrochloric acid, nitric acid, sulfuric acid, phosphoric acid, hydrobromic acid and the like.

Examples of the salt with an organic acid include salts with oxalic acid, maleic acid, citric acid, fumaric acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid and the like.

Examples of the salt with an inorganic base include sodium salt, potassium salt, calcium salt, magnesium salt, ammonium salt and the like.

Examples of the salt with an organic base include methylamine, diethylamine, trimethylamine, triethylamine, ethanolamine, diethanolamine, triethanolamine, ethylenediamine, tris(hydroxymethyl)methylamine, dicyclohexylamine, N,N'-dibenzylethylenediamine, guanidine, pyridine, picoline, choline, cinchonine, meglumine and the like.

Examples of the salt with an amino acid include salts with lysine, arginine, aspartic acid, glutamic acid and the like.

The salt of compound (I) (or the salt of the compound (I-h)) of the present invention is preferably a salt with an inorganic base or an organic base.

A solvate of the compound (I) (or compound (I-h)) of the present invention or a salt thereof is the compound (I) (or compound (I-h)) of the present invention or a salt thereof coordinated with a solvent molecule, and also encompasses a hydrate. Examples thereof include hydrate, ethanol solvate, dimethyl sulfoxide solvate and the like of the compound (I) (or compound (I-h)) of the present invention or a salt thereof.

Each group of the compound (I) of the present invention is explained below.

$R^1$, $R^{1'}$, $R^2$, $R^{2'}$, $R^3$, $R^{3'}$, $R^4$ and $R^{4'}$ are each independently a hydrogen atom, a halogen atom, an optionally substituted alkyl group, an optionally substituted cycloalkyl group, an optionally substituted alkoxy group, an optionally substituted alkylthio group, a tri-substituted silyl group, a tri-substituted siloxy group or an optionally substituted acyloxy group.

$R^1$, $R^{1'}$, $R^2$, $R^{2'}$, $R^3$, $R^{3'}$, $R^4$ and $R^{4'}$ are preferably each independently a hydrogen atom, a halogen atom, an optionally substituted alkyl group, an optionally substituted alkoxy group, a trialkylsilyl group or a trialkylsiloxy group, more preferably, each independently a hydrogen atom, a halogen atom, a $C_{1-6}$ alkyl group optionally substituted by halogen atom(s), a $C_{1-6}$ alkoxy group optionally substituted by halogen atom(s), a tri $C_{1-6}$ alkylsilyl group or a tri $C_{1-6}$ alkylsiloxy group, and a hydrogen atom or a halogen atom is particularly preferable.

In $R^1$, $R^{1'}$, $R^2$, $R^{2'}$, $R^3$, $R^{3'}$, $R^4$ and $R^{4'}$, each of $R^1$ and $R^{1'}$, $R^2$ and $R^{2'}$, $R^3$ and $R^{3'}$, and $R^4$ and $R^{4'}$ are preferably the same group. All of $R^1$, $R^{1'}$, $R^2$, $R^{2'}$, $R^3$, $R^{3'}$, $R^4$ and $R^{4'}$ may be the same group.

X is a carboxy group amidated or esterified by condensation with an optically active chiral compound. Examples of the optically active chiral compound include the compounds exemplified above.

X is preferably a carboxy group amidated by condensation with an optically active chiral amine. Examples of the optically active chiral amine include 1-phenylethylamine, 1-cyclohexylethylamine, 1-(1-naphthyl)ethylamine, 1-(2-naphthyl)ethylamine, sec-butylamine, 1-phenyl-2-(p-tolyl)ethylamine, 1-(p-tolyl)ethylamine, 1-(4-methoxyphenyl)ethylamine, β-methylphenethylamine, 2-amino-1-butanol, 2-amino-1,2-diphenylethanol, 1-amino-2-indanol, 2-amino-1-phenyl-1,3-propanediol, 2-amino-1-propanol, leucinol, phenylalaninol, 2-phenylglycinol, valinol, norephedrine, methioninol, 1-benzyl-3-aminopyrrolidine, 2-(methoxymethyl)pyrrolidine, 1-(2-pyrrolidinomethyl)pyrrolidine, an amino acid having a protected carboxy group and the like, from the compounds exemplified above as an optically active form.

X is more preferably a carboxy group amidated by condensation with (R)-(+)-1-phenylethylamine or (S)-(−)-1-phenylethylamine.

n is an integer of not less than 10, preferably an integer of not less than 100 and not more than 10000.

As the compound (I) of the present invention, the following compound is preferable.

[Compound (IA)]

Compound (I) wherein $R^1$, $R^{1'}$, $R^2$, $R^{2'}$, $R^3$, $R^{3'}$, $R^4$ and $R^{4'}$ are each independently a hydrogen atom, a halogen atom, an optionally substituted alkyl group, an optionally substituted alkoxy group, a trialkylsilyl group or a trialkylsiloxy group, and each of $R^1$ and $R^{1'}$, $R^2$ and $R^{2'}$, $R^3$ and $R^{3'}$, and $R^4$ and $R^{4'}$ is the same group;

X is a carboxy group amidated by condensation with an optically active chiral amine (e.g., an optically active form of 1-phenylethylamine, 1-cyclohexylethylamine, 1-(1-naphthyl)ethylamine, 1-(2-naphthyl)ethylamine, sec-butylamine, 1-phenyl-2-(p-tolyl)ethylamine, 1-(p-tolyl)ethylamine, 1-(4-methoxyphenyl)ethylamine, β-methylphenethylamine, 2-amino-1-butanol, 2-amino-1,2-diphenylethanol, 1-amino-2-indanol, 2-amino-1-phenyl-1,3-propanediol, 2-amino-1-propanol, leucinol, phenylalaninol, 2-phenylglycinol, valinol, norephedrine, methioninol, 1-benzyl-3-aminopyrrolidine, 2-(methoxymethyl)pyrrolidine, 1-(2-pyrrolidinomethyl)pyrrolidine, an amino acid having a protected carboxy group and the like); and n is an integer of not less than 10.

More preferable compound (I) is the following compound.

[Compound (IB)]

Compound (I) wherein $R^1$, $R^{1'}$, $R^2$, $R^{2'}$, $R^3$, $R^{3'}$, $R^4$ and $R^{4'}$ are each independently a hydrogen atom, a halogen atom, a $C_{1-6}$ alkyl group optionally substituted by halogen atom(s), a $C_{1-6}$ alkoxy group optionally substituted by halogen atom(s), a tri $C_{1-6}$ alkylsilyl group or a tri $C_{1-6}$ alkylsiloxy group, and each of $R^1$ and $R^{1'}$, $R^2$ and $R^{2'}$, $R^3$ and $R^{3'}$, and $R^4$ and $R^{4'}$ are the same group;

X is a carboxy group amidated by condensation with an optically active chiral amine (compounds exemplified above); and n is an integer of not less than 10 and not more than 10000.

More preferable compound (I) is the following compound.

[Compound (IC)]

Compound (I) wherein $R^1$, $R^{1'}$, $R^2$, $R^{2'}$, $R^3$, $R^{3'}$, $R^4$ and $R^{4'}$ are each independently a hydrogen atom or a halogen atom, and each of $R^1$ and $R^{1'}$, $R^2$ and $R^{2'}$, $R^3$ and $R^{3'}$, and $R^4$ and $R^{4'}$ are the same group;

X is a carboxy group amidated by condensation with (R)-(+)-1-phenylethylamine or (S)-(−)-1-phenylethylamine; and n is an integer of not less than 100 and not more than 10000.

Of the compounds (I) of the present invention, compound (I-h) having a one-handed helical structure in the main chain as a secondary structure thereof is more preferable, and compound (IA-h), compound (IB-h) and compound (IC-h) having a one-handed helical structure in the main chain of the above-mentioned compound (IA), compound (IB) and compound (IC), respectively, are particularly preferable.

The number average degree of polymerization (average number of diphenylethylene units contained in one molecule) of the compound (I) or compound (I-h) of the present invention is not less than 10, preferably not less than 100 and does not have a particular upper limit. However, it is desirably not more than 10000 for easy handling.

The compound (I) or compound (I-h) of the present invention may be labeled with an isotope (e.g., $^3H$, $^2H(D)$, $^{14}C$, $^{35}S$ etc.).

(Synthesis of the Compound (I) and Compound (I-h) of the Present Invention)

While the production method of the compound (I) and compound (I-h) of the present invention is not particularly limited, for example, the compound (I) can be synthesized via the following reactions.

Unless otherwise specified, the starting compound is easily available as a commercially available product, or can be produced according to a method known per se or a method analogous thereto.

The compounds obtained in each step in the following reaction scheme can also be used for the next reaction directly as a reaction mixture or a crude product. Alternatively, the compound can also be isolated from a reaction mixture according to a conventional method, and can be easily purified by a general separation means such as recrystallization, distillation, chromatography and the like.

Compound (I) and compound (I-h) of the present invention can be produced, for example, by the following steps.

[wherein Y and Y' are each a leaving group such as a halogen atom, a trifluoromethanesulfonyloxy group and the like, $R^7$ and $R^{7'}$ are each an optionally substituted alkyl group, an optionally substituted aryl group, or an optionally substituted aralkyl group, and other symbols are as defined above].

Step 1

In this step, compound 1 is esterified to produce compound 2.

The reaction is performed by a method known per se (e.g., a method of converting to acid halide and reacting same with alcohol ($R^7OH$), a method of reacting with alcohol ($R^7OH$) in the presence of a condensing agent and a base, etc.).

Examples of the halogenating agent to be used for conversion to acid halide include thionyl chloride, oxalyl chloride and the like.

Examples of the solvent include aromatic hydrocarbons such as toluene, xylene and the like; ethers such as diethyl ether, tetrahydrofuran, dioxane and the like; halogenated hydrocarbons such as chloroform, dichloromethane and the like and the like and a mixture thereof.

The reaction temperature is generally −10° C.-30° C., preferably 0°×C.-20° C., and the reaction time is generally 1-30 hr.

Examples of the condensing agent include dicyclohexylcarbodiimide (DCC), diisopropylcarbodiimide (DIC), N-ethyl-N'-[3-(dimethylamino)propyl]carbodiimide and hydrochloride thereof (EDC.HCl), (benzotriazol-1-yloxy)tripyrrolidinophosphonium hexafluorophosphate (PyBop), O-(benzotriazol-1-yl)-N,N,N',N'-tetramethyluronium tetrafluoroborate (TBTU), 1-[bis(dimethylamino)methylene]-5-chloro-1H-benzotriazolium 3-oxide hexafluorophosphate (HCTU), O-benzotriazole-N,N,N',N'-tetramethyluronium hexafluoroborate (HBTU) and the like.

The amount of the condensing agent to be used is 1-10 equivalents, preferably 1-5 mol, relative to compound 1 (1 equivalent).

Examples of the solvent include aromatic hydrocarbons such as toluene, xylene and the like; ethers such as diethyl ether, tetrahydrofuran, dioxane and the like; halogenated hydrocarbons such as chloroform, dichloromethane and the like and the like and a mixture thereof. Of these, toluene, tetrahydrofuran and the like are preferable.

The reaction temperature is generally −10° C.-30° C., preferably 0° C.-20° C., and the reaction time is generally 1-30 hr.

Step 2

In this step, a leaving group Y (preferably iodine) of compound 2 is substituted by a trimethylsilylethynyl group under Sonogashira coupling conditions to convert same to compound 3.

The reaction is performed using a metal catalyst in a solvent that does not influence the reaction in the presence of a base.

Examples of the metal catalyst include palladium compounds such as tetrakis(triphenylphosphine)palladium(0) (Pd(PPh$_3$)$_4$), tris(dibenzylideneacetone)dipalladium(0) (Pd$_2$(dba)$_3$), dichloro bis(triphenylphosphine) palladium(II) (Pd(PPh$_3$)$_2$Cl$_2$), dichloro bis(acetonitrile) palladium(II) ((CH$_3$CN)$_2$PdCl$_2$) and the like. Of these, dichloro bis(triphenylphosphine)palladium(II) is preferable.

The amount of the metal catalyst to be used is generally 0.001-1 equivalent relative to compound 2 (1 equivalent).

Examples of the base include organic bases such as triethylamine and the like, inorganic bases such as ammonia and the like. Of these, triethylamine is preferable.

The base can also be used as a solvent. The amount of the base to be used is generally 10-1000 equivalents relative to compound 2 (1 equivalent).

In this step, additives such as copper compounds (copper iodide, copper bromide and the like), phosphine compounds (2-dicyclohexylphosphino-2',4',6'-triisopropylbiphenyl and the like) and the like may be added as necessary.

Examples of the solvent include etheric solvents such as tetrahydrofuran, 1,4-dioxane and the like, polar solvents such as acetonitrile, dimethylformamide and the like, and hydrocarbon solvents such as benzene and the like. Of these, tetrahydrofuran is preferable.

The reaction temperature is generally −10° C.-100° C., preferably 0° C.-50° C.

The reaction time is generally 0.5-24 hr.

Step 3

In this step, a trimethylsilyl group of compound 3 is removed to convert same to compound 4.

The reaction is performed using a base or a fluoride ion source such as tetra-n-butylammonium fluoride and the like in a solvent that does not influence the reaction.

Examples of the base include inorganic bases such as potassium carbonate, cesium carbonate, sodium carbonate and the like. Of these, potassium carbonate is preferable.

The amount of the base to be used is generally 1-10 equivalents relative to compound 3 (1 equivalent).

Examples of the solvent include etheric solvents such as tetrahydrofuran (THF), diethyl ether, tert-butyl methyl ether, diisopropyl ether, ethylene glycol-dimethylether (DME), diethylene glycol dimethylether (diglyme) and the like, alcoholic solvents such as methanol, ethanol and the like, mixed solvents such as tetrahydrofuran and methanol, DME and methanol, and the like. Of these, a mixed solvent of tetrahydrofuran and methanol is preferable.

The reaction temperature is generally −20° C.-100° C., preferably −10° C.-40° C.

The reaction time is generally 0.5-24 hr.

Step 4

In this step, a coupling reaction of a leaving group Y' (preferably iodine) of compound 2' and compound 4 is performed under Sonogashira coupling conditions to convert same to compound 5.

The coupling reaction can be performed in the same reaction form and reaction conditions as in step 2.

Step 5

In this step, compound 5 is converted to compound 6 by polymerization.

The reaction is performed using a metal catalyst under a nitrogen atmosphere in a solvent that does not influence the reaction.

Preferred as the metal catalyst is a mixed catalyst of tungsten (VI) chloride and tetraphenyltin (IV).

The amount of the metal catalyst to be used is generally 0.0001-0.2 equivalent, preferably 0.001-0.1 equivalent, relative to compound 5 (1 equivalent).

Examples of the solvent include aromatic hydrocarbons such as toluene, xylene and the like; ethers such as tetrahydrofuran, dioxane and the like and the like and a mixture thereof. Of these, toluene and the like are preferable.

The amount of the solvent to be used in the step is, for example, preferably an amount that sets the concentration of compound 5 to about 0.001-1M, particularly preferably about 0.1-0.5M.

The reaction temperature is generally −10° C.-200° C., preferably 10° C.-120° C.

The reaction time is generally 0.5-30 hr.

Step 6

In this step, ester of compound 6 is hydrolyzed to convert same to compound (II).

The reaction is performed using a base in a solvent that does not influence the reaction.

Examples of the base include inorganic bases such as potassium hydroxide, sodium hydroxide and the like. Of these, potassium hydroxide is preferable.

The amount of the base to be used is generally 1-100 equivalents relative to compound 6 (1 equivalent).

Examples of the solvent include mixed solvents of etheric solvents such as tetrahydrofuran (THF), diethyl ether, tert-butyl methyl ether, diisopropyl ether, ethylene glycol-dimethylether (DME), diethylene glycol dimethylether (diglyme) and the like, and water, and the like. Of these, a mixed solvent of tetrahydrofuran and water is preferable.

The reaction temperature is generally 0° C.-100° C., preferably 10° C.-80° C.

The reaction time is generally 0.5-30 hr.

Step 7

In this step, a carboxy group of compound (II) is amidated or esterified by a condensation reaction with an optically active chiral compound to convert same to compound (I).

The esterification can be performed by using a reaction form and reaction conditions similar to those in step 1 except that optically active chiral alcohol (preferably, for example, 1-phenylethyl alcohol, 1-phenyl-2-propanol, 1,2,3,4-tetrahydro-1-naphthol, 1-acetyl-3-pyrrolidinol, 1-benzyl-3-pyrrolidinol, 2-butanol, α-hydroxy-γ-butyrolactone, 3-hydroxytetrahydrofuran, 1-methyl-3-pyrrolidinol, 2-octanol, 2-pentanol, 1-(2-naphthyl)ethanol, menthol, borneol, quinidine, quinine, quincorine, quincoridine, cinchonidine, cinchonine etc. from the aforementioned compounds exemplified as the optically active chiral compound) is used as alcohol.

The amidation is performed by a method including reacting compound (II) and an optically active chiral amine (preferably, the compounds exemplified above) according to a method known per se, in the presence of a condensing agent, and the like.

The reaction is performed in a solvent that does not influence the reaction and by using a condensing agent in the presence of a condensation additive as necessary.

Examples of the condensation additive include 1-hydroxybenzotriazole (HOBt), ethyl 1-hydroxy-1H-1,2,3-triazole-5-carboxylate (HOCt), 1-hydroxy-7-azabenzotriazole (HOAt) and the like.

The amount of the condensation additive to be used is preferably 0.05-1.5 equivalents relative to 1 equivalent of the compound (II).

Examples of the condensing agent include 4-(4,6-dimethoxy-1,3,5-triazin-2-yl)-4-methylmorpholinium chloride (DMT-MM), dicyclohexylcarbodiimide (DCC), diisopropylcarbodiimide (DIC), N-ethyl-N'-[3-(dimethylamino)propyl]carbodiimide and its hydrochloride (EDC.HCl), (benzotriazol-1-yloxy)tripyrrolidinophosphonium hexafluorophosphate (PyBop), O-(benzotriazol-1-yl)-N,N,N',N'-tetramethyluronium tetrafluoroborate (TBTU), 1-[bis(dimethylamino)methylene]-5-chloro-1H-benzotriazolium-3-oxide hexafluorophosphate (HCTU), O-benzotriazole-N,N,N',N'-tetramethyluronium hexafluoroborate (HBTU) and the like. DMT-MM usable even in an aqueous solvent is particularly preferable.

The amount of the condensing agent to be used is 1-10 equivalents, preferably 1-5 equivalents, relative to 1 equivalent of the compound (II).

Examples of the solvent include water; dimethyl sulfoxide (DMSO); aromatic hydrocarbons such as toluene, xylene and the like; ethers such as diethyl ether, tetrahydrofuran, dioxane and the like; halogenated hydrocarbons such as chloroform, dichloromethane and the like and the like, and a mixture thereof. Of these, a mixed solvent of water and DMSO, and the like are preferable.

The reaction temperature is generally 0-40° C., preferably 0° C.-room temperature. The reaction time is generally 1-30 hr.

Step 8

In this step, a one-handed helical structure is formed in the main chain of compound (I) to convert same to compound (I-h).

The reaction is performed by heat treating compound (I) in a solvent that does not influence the reaction.

Examples of the solvent include dimethyl formamide (DMF), dimethyl sulfoxide (DMSO), dimethyl acetamide (DMA), or a mixed solvent thereof, and a DMF/DMSO mixed solvent is preferable.

The reaction temperature is generally 10° C.-200° C., preferably 80° C.-100° C. and the reaction time is generally 1-30 hr.

Whether a one-handed helical chirality has been induced in compound (I) (that is, whether compound (I-h) has been formed) can be confirmed by measuring CD and UV spectra.

With what optical purity the one-handed helical chirality has been induced in compound (I) (lopsided degree of helical chirality of compound (I-h)) can be confirmed by measuring the peak intensity ($\Delta\epsilon$) of CD spectrum. That is, the higher the peak intensity is, the more lopsided toward one direction the winding direction of the helix is.

(Chiral Column Packing Material Supporting Compound (I) or Compound (I-h) of the Present Invention, and Production Method of Chiral Column Packed with the Packing Material for High Performance Liquid Chromatography)

While the compound (I) or compound (I-h) of the present invention itself can be directly used as an optical isomer separating agent, generally, it is preferably supported by carriers such as porous organic carrier, porous inorganic carrier or the like.

The most preferable carrier to be used in the present invention is silica gel. The particle size of silica gel is 0.1 μm-300 μm, preferably 1 μm-10 μm, and the average pore size is 10 Å-100 μm, preferably 50 Å-50000 Å.

A most convenient method of supporting compound (I) or compound (I-h) of the present invention on silica gel is a method including dissolving the compound (I) or compound (I-h) of the present invention in an acetone/tetrahydrofuran mixed solvent, and coating silica gel with the solution to support compound (I) or compound (I-h).

The amount of the compound (I) or compound (I-h) of the present invention carried on silica gel can be confirmed by using thermogravimetric analysis.

A chiral column can be prepared by packing a column with silica gel supporting the compound (I) or compound (I-h) of the present invention by a slurry method (preferred as the solvent is hexane).

EXAMPLES

The present invention is explained in more detail by referring to Examples; however, the present invention is not limited thereby.

The reaction was monitored by thin layer chromatography using Merck 60 F254 silica gel plate (thickness 0.25 mm).

$^1$H and $^{13}$C-NMR spectra were measured by using JEOL ECA500, and deuterated chloroform, deuterated dimethyl sulfoxide and deuterium oxide as solvents. $^1$H-NMR data are reported in chemical shift (δ ppm), multiplicity (s=singlet, d=doublet, t=triplet, q=quartet, quint=quintet, m=multiplet, dd=double doublet, dt=double triplet, brs=broad singlet), coupling constant (Hz), integration and allocation.

Flash chromatography was performed by using silica gel 60N of Kanto Chemical Co., Inc. (Japan, Tokyo).

The average molecular weight was calculated based on polystyrene, by gel permeation chromatography (high performance liquid chromatography pump PU-2080 manufactured by JASCO Corporation, ultraviolet visible detector UV-970 manufactured by JASCO Corporation, column oven CO-1560 manufactured by JASCO Corporation, column KF-805L manufactured by Shodex).

For the measurement of the separation ability of the prepared compound (I) of the present invention, high performance liquid chromatography pump PU-2080 manufactured by JASCO Corporation, ultraviolet visible detector MD-910 manufactured by JASCO Corporation, and optical rotation detector OR-990 manufactured by JASCO Corporation were used. Circular dichroism (CD) was measured by using circular dichroism dispersion meter J-725 manufactured by JASCO Corporation, ultraviolet visible absorption was measured by using ultraviolet visible spectrophotometer V-570 manufactured by JASCO Corporation, and infrared absorption was measured by using infrared spectrophotometer FT/IR-460 manufactured by JASCO Corporation.

The "room temperature" in the following Examples generally shows about 10° C. to about 25° C. The ratio indicated for the mixed solvent shows, unless otherwise specified, a volume mixing ratio. % shows wt % unless otherwise specified.

Example 1

Synthesis of Compound (Ia)

(1) Synthesis of heptyl 4-iodobenzoate (2a)

Under a nitrogen atmosphere, 4-iodobenzoic acid (Ia) (10.6 g, 42.9 mmol) was dissolved in anhydrous dichloromethane (140 mL), and several drops of anhydrous N,N-dimethylformamide were added. Thereafter, oxalyl chloride (4.50 mL, 42.4 mmol) was added at 0° C., and the mixture was stirred at room temperature for 10 hr. The solvent was removed, anhydrous pyridine (70 mL) and n-heptanol (7.0 mL, 49.4 mmol) were added, and the mixture was stirred at 70° C. for 5 hr. The reaction solvent was removed, the residue was diluted with ethyl acetate, washed with distilled water and saturated aqueous sodium hydrogen carbonate solution, and the organic layer was dried over anhydrous sodium sulfate. The solvent was removed under reduced pressure, and the residue was purified by column chromatography (ethyl acetate:hexane=1:19) to give heptyl 4-iodobenzoate (2a) (14.5 g, yield 97%) as an oily liquid.

(2) Synthesis of heptyl 4-[(trimethylsilyl)ethynyl]benzoate (3a)

Under a nitrogen atmosphere, heptyl 4-iodobenzoate (2a) (10.1 g, 29.3 mmol) was dissolved in anhydrous triethylamine (50 mL), Pd(PPh$_3$)$_2$Cl$_2$ (0.0820 g, 0.117 mmol), triphenylphosphine (0.126 g, 0.480 mmol), copper (I) iodide (0.135 g, 0.192 mmol), and trimethylsilylacetylene (TMSA) (4.30 mL, 31.7 mmol) were added, and the mixture was stirred at room temperature for 20 hr. The reaction solution was filtered through celite, the solvent was removed under reduced pressure, and the residue was purified by column chromatography (ethyl acetate:hexane=1:30) to give heptyl 4-[(trimethylsilyl)ethynyl]benzoate (3a) (9.23 g, yield 98%) as an oily liquid.

(3) Synthesis of heptyl 4-ethynylbenzoate (4a)

Heptyl 4-[(trimethylsilyl)ethynyl]benzoate (3a) (10.4 g, 32.8 mmol) was dissolved in tetrahydrofuran/methanol (3/1, v/v) (400 mL), potassium carbonate (1.00 g, 7.24 mmol) was added, and the mixture was stirred at −10° C. for 1 hr. The reaction solvent was concentrated, and the residue was diluted with ethyl acetate, washed with 1N hydrochloric acid and saturated aqueous sodium hydrogen carbonate solution, and the organic layer was dried over anhydrous sodium sulfate. The solvent was removed under reduced pressure, and the residue was purified by column chromatography (ethyl acetate:hexane=1:25) to give heptyl 4-ethynylbenzoate (4a) (6.58 g, yield 82%) as an oily liquid.

(4) Synthesis of bis[4-(heptyloxycarbonyl)phenyl]acetylene (5a)

Under a nitrogen atmosphere, heptyl 4-iodobenzoate (2a) (3.64 g, 10.5 mmol) was dissolved in anhydrous triethylamine (8.6 mL), and anhydrous tetrahydrofuran (4.0 mL), triphenylphosphine (39.3 mg, 0.150 mmol), copper (I) iodide (43.8 mg, 0.230 mmol), and $Pd(PPh_3)_2Cl_2$ (27.9 mg, 0.0397 mmol) were added. Thereafter, a solution of heptyl 4-ethynylbenzoate (4a) (2.64 g, 10.8 mmol) in anhydrous tetrahydrofuran (2.0 mL) was slowly added dropwise, and the mixture was stirred at room temperature for 3 hr. The reaction solution was filtered through celite and, after removal under reduced pressure, diluted with ethyl acetate, washed with water and saturated brine, and the organic layer was dried over anhydrous sodium sulfate. The solvent was removed under reduced pressure, and the residue was purified by column chromatography (ethyl acetate:hexane=1:10). Subsequent recrystallization from methanol/ethanol (5:1, v/v) gave bis[(4-heptyloxycarbonyl)phenyl]acetylene (5a) (4.64 g, yield 95%) as a white solid.

mp: 61.3-62.4° C.;

IR (KBr, cm$^{-1}$): 1943 (C≡C), 1707 (C=O);

$^1$H NMR (500 MHz, $CDCl_3$, rt): δ 8.04 (d, J=8.6 Hz, 4H, Ar—H), 7.60 (d, J=8.0 Hz, 4H, Ar—H), 4.33 (t, J=6.6 Hz, 4H, 2OCH$_2$CH$_2$), 1.76 (quint, J=6.6 Hz, 4H, 2OCH$_2$CH$_2$), 1.25-1.47 (m, 16H, 8CH$_2$), 0.90 (t, J=6.9 Hz, 6H, 2CH$_3$);

$^{13}$C NMR (125 MHz, $CDCl_3$, rt): δ 166.19, 131.76, 130.46, 129.68, 127.38, 91.49, 65.56, 31.88, 29.11, 28.85, 26.15, 22.75, 14.23;

Elemental analysis: Calcd for $C_{30}H_{38}O_4$: C, 77.89; H, 8.28.
Found: C, 77.60; H, 8.37.

(5) Synthesis of Compound (6a) by Polymerization of Compound (5a)

Under a nitrogen atmosphere, bis[(4-heptyloxycarbonyl) phenyl)]acetylene (5a) (600 mg, 1.30 mmol), tungsten (VI) chloride (51.6 mg, 0.130 mmol), and tetraphenyltin (IV) (55.5 mg, 0.130 mmol) were charged in a Schlenk tube, and anhydrous toluene (2.6 mL) distilled in vacuo was added. Thereafter, the mixture was stirred at 110° C. for 24 hr. After cooling to room temperature, the mixture was reprecipitated in a large amount of methanol and centrifuged to give a yellow ocher solid. Then, the solid was dissolved in a small amount of toluene, reprecipitated in a large amount of a mixed solvent of tetrahydrofuran/methanol (3:1, v/v), and poly(diphenylacetylene)heptyl ester (compound (6a)) (404 mg, yield 67%) was recovered by centrifugation as a yellow ocher solid. The number average molecular weight $M_n$ of compound (6a) calculated based on polystyrene as measured by gel permeation chromatography measurement was 1.46× 10$^4$ and the dispersity $M_w/M_n$ was 1.58.

IR (KBr, cm$^{-1}$): 1721 (C=O);

$^1$H NMR (500 MHz, CDCl$_3$, 50° C.): δ 7.16-7.28 (br, 4H, Ar—H), 6.41-6.71 (br, 2H, Ar—H), 5.92-6.15 (br, 2H, Ar—H), 4.03-4.48 (br, 4H, 2OCH$_2$CH$_2$), 1.60-1.93 (br, 4H, 2OCH$_2$CH$_2$), 1.25-1.47 (br, 16H, 8CH$_2$), 0.79-1.04 (br, 6H, 2CH$_3$);

Elemental analysis: Calcd for C$_{30}$H$_{38}$O$_4$: C, 77.89; H, 8.28.
Found: C, 77.40; H, 8.42.

(6) Synthesis of Compound (IIa) by Hydrolysis of Compound (6a)

Compound (6a) (400 mg) was dissolved in tetrahydrofuran (15 mL), 4N aqueous potassium hydroxide solution (35 mL) was added, and the mixture was stirred at 80° C. for 2 hr. Thereafter, tetrahydrofuran was evaporated, 4N aqueous potassium hydroxide solution (30 mL) was added, and the mixture was stirred at 80° C. for 24 hr. Distilled water was added to the reaction solution, and the mixture was washed with diethyl ether and chloroform. The aqueous layer was acidified with 1N aqueous hydrochloric acid solution, and the precipitated solid was collected by centrifugation, and thereafter washed with distilled water to give poly(diphenylacetylene)carboxylic acid (optically inactive form) (compound (IIa)) (180 mg, yield 78%) as a brown solid.

IR (KBr, cm$^{-1}$): 1701 (C=O);

$^1$H NMR (500 MHz, d$_6$-DMSO/D$_2$O (1:1, v/v), 80° C.): δ 7.19-6.88 (br, 4H, Ar—H), 6.53-6.31 (br, 2H, Ar—H), 6.12-5.82 (br, 2H, Ar—H);

Elemental analysis: Calcd for (C$_{16}$H$_{10}$O$_4$·2.1H$_2$O)$_n$: C, 63.20; H, 4.71. Found: C, 63.04; H, 4.55.

(7) Synthesis of Compound (Ia) by Condensation of Compound (IIa) and (S)-(−)-1-phenylethylamine Compound (IIa) (120 mg, 0.451 mmol) was dissolved in dimethyl sulfoxide/water (5:1, v/v) (21 mL), (S)-(−)-1-phenylethylamine (223 μL, 1.88 mmol) and DMT-MM (520 mg, 1.88 mmol) were added, and the mixture was stirred at room temperature for 16 hr. The reaction solution was reprecipitated in a large amount of a hexane/ethanol (5:1, v/v) mixed solvent, recovered by centrifugation and washed with hexane to give compound (Ia) (125 mg, yield 60%) as a yellow solid.

(8) Synthesis of Optically Active Compound (Ia-h) Having a One-Handed Helical Structure by Heat Treatment of Compound (Ia)

Ia

Figure 1:
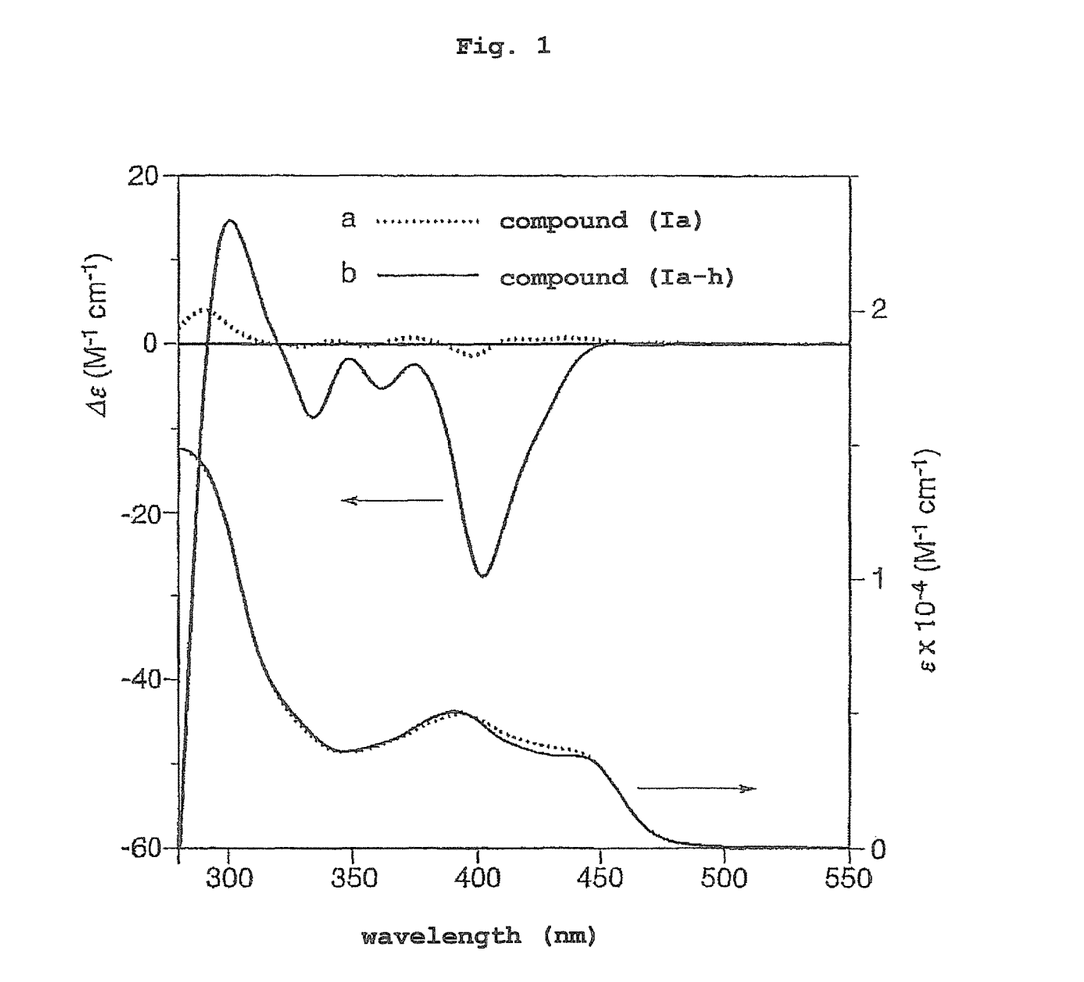

Compound (Ia) (150 mg) obtained in the aforementioned (7) was dissolved in dimethyl sulfoxide/N,N-dimethylformamide (2:1, v/v) (16 mL), and the mixture was heated at 90° C. for 15 hr. The reaction mixture was concentrated, reprecipitated in a large amount of methanol, and centrifuged to give compound (Ia-h) (147 mg) at a yield of 98%. The obtained compound (Ia-h) was dissolved in dimethyl sulfoxide/N,N-dimethylformamide (2:1, v/v), and CD and UV spectra were measured. The results are shown in FIG. 1. It was confirmed that strongly-induced CD is expressed in an absorption region in the main chain by heating at 90° C. It could be confirmed that this induced a one-handed helical structure in compound (Ia), and optically active compound (Ia-h) having a one-handed helical structure was produced.

Example 2

Preparation of Column and Evaluation of Asymmetric Discrimination Ability (1) Preparation of Chiral Column (A) for Optical Resolution Supporting Compound (Ia)

Compound (Ia) (150 mg) was dissolved in acetone/tetrahydrofuran (4:1, v/v) (5 mL), filtered through a membrane filter (0.2 μm) and supported on silica gel for HPLC (manufactured by DAISO CO., LTD.: particle size 7 μm). The obtained polymer supporting gel was packed in a stainless column (length 25 cm, inner diameter 0.20 cm) by the slurry method (solvent: hexane).

(2) Preparation of Chiral Column (B) Supporting Compound (Ia-h) for Optical Resolution Compound (Ia-h) (150 mg) was dissolved in acetone/tetrahydrofuran (2:1, v/v) (5 mL), filtered through a membrane filter (0.2 μm) and supported on silica gel for HPLC (manufactured by DAISO CO., LTD.: particle size 7 μm). The obtained polymer supporting gel was packed in a stainless column (length 25 cm, inner diameter 0.20 cm) by a slurry method (solvent: hexane).

(3) Optical Resolution of 1,1'-bi-2-naphthol Using Chiral Columns (A) and (B)

Figure 2:
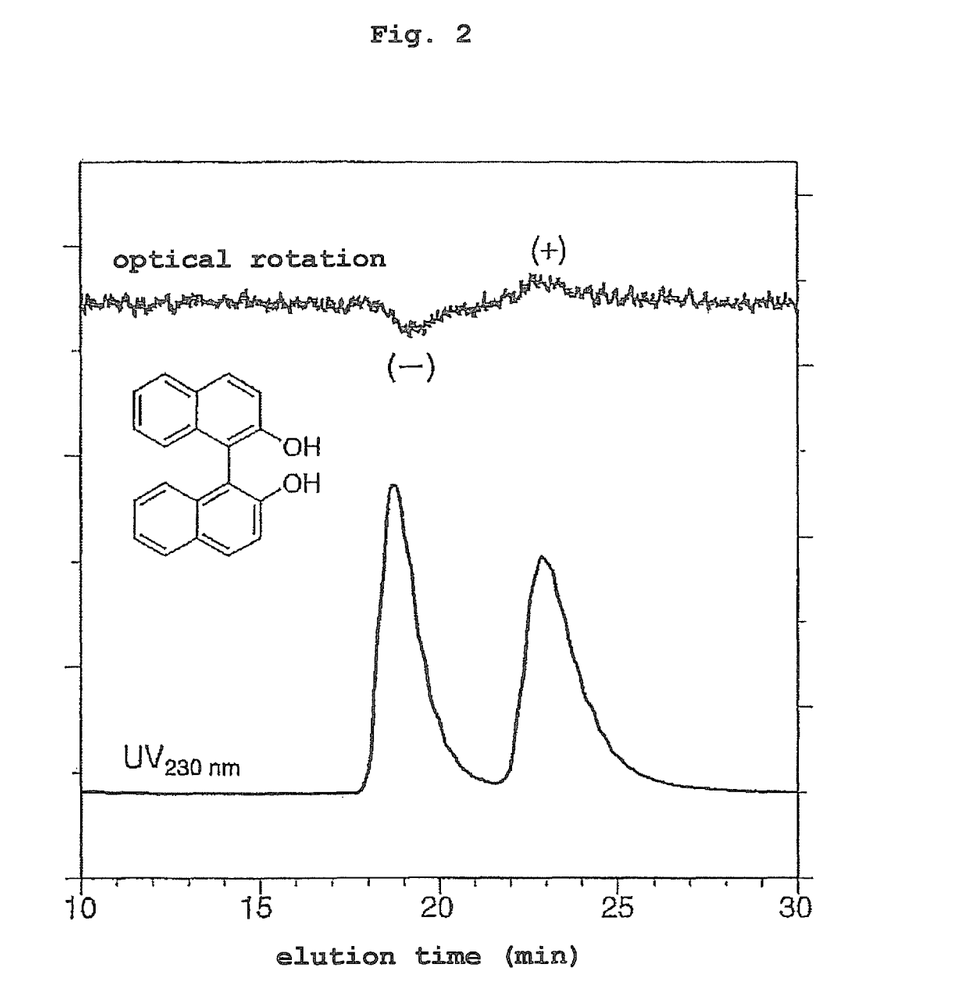
FIG. 2 shows chiral separation chromatogram (flow rate: 0.1 mL/min, eluent: hexane/2-propanol (90:10, v/v)) of a racemate of 1,1'-bi-2-naphthol by using chiral column (B) obtained in Example 2 (2).

Using the chiral columns (A) and (B) prepared by the operations of the above-mentioned (1) and (2), optical resolution of racemate of 1,1'-bi-2-naphthol was performed by HPLC (room temperature: about 20° C.). The eluent used was hexane/2-propanol=90/10 (v/v), and the flow rate was 0.1 mL/min. The time $t_0$ necessary for the eluent to pass through the column was determined from the elution time of 1,3,5-tri-tert-butylbenzene. As a result, when chiral column (A) was used, $k_1$=1.52, α=1.34 were estimated, and when chiral column (B) was used, $k_1$=0.80, α=1.53 were estimated (Table 1, FIG. 2 (results of separation by chiral column (B))).

(3) Confirmation of Asymmetric Discrimination Ability of Chiral Columns (A) and (B) by HPLC Using the chiral columns (A) and (B) prepared by the operations of the above-mentioned (1) and (2), optical resolutions of racemates of various compounds were performed by HPLC (flow rate 0.1 mL/min (hexane/2-propanol=90/10 or 99/1). The separation conditions and the results are shown in Table 1. While optical resolution is possible by using any column, the separation coefficient (α) value increased when chiral column (B) was used. Thus, it could be confirmed that induction of helical chirality in the main chain by a heat treatment more remarkably improves the optical resolution ability.

TABLE 1

|  |  |  | chiral column (A) | | chiral column (B) | |
| --- | --- | --- | --- | --- | --- | --- |
| No. | racemate | eluent | $k_1$* | separation coefficient α** | $k_1$* | separation coefficient α** |
| 1 | O ... Ph (2-phenylcyclohexanone) | hexane/ 2-propanol = 99/1 | 1.05 | 1.14 | 0.36 | 1.35 (−) |

TABLE 1-continued

| No. | racemate | eluent | chiral column (A) $k_1$* | chiral column (A) separation coefficient α** | chiral column (B) $k_1$* | chiral column (B) separation coefficient α** |
|---|---|---|---|---|---|---|
| 2 | (cyclopropane with two CONHPh groups) | hexane/2-propanol = 90/10 | 0.47 | 1.64 (+) | 0.12 | 1.98 (+) |
| 3 | (binaphthol) | hexane/2-propanol = 90/10 | 1.52 | 1.34 (−) | 0.80 | 1.53 (−) |
| 4 | (3,3'-diphenyl binaphthol) | hexane/2-propanol = 90/10 | 1.39 | 1.47 | 0.78 | 1.62 (n.d.) |
| 5 | (anthracenyl-CHOH-CF₃) | hexane/2-propanol = 99/1 | 10.5 | 1 | 4.14 | 1.2 (n.d.) |
| 6 | (cyclobutane with two CONHPh groups) | hexane/2-propanol = 90/10 | 1.02 | 1 | 0.60 | 1.39 (+) |
| 7 | Co(acac)₃ | hexane/2-propanol = 90/10 | 5.95 | 1 | 3.37 | 1.54 (−) |
| 8 | Cr(acac)₃ | hexane/2-propanol = 90/10 | — | — | 2.80 | 1.69 (+) |

*$k_1$: retention factor of enantiomer eluted first
**symbol in parentheses is optical rotation of enantiomer eluted earlier As used herein, the retention factor $k_1$ is an index showing the degree of strength of the interaction between an enantiomer eluted first and the packing material. To be specific, it is calculated by the formula represented by: $k_1=(t_1-t_0)/t_0$ (wherein $t_1$ is elution time of enantiomer which is eluted first, and $t_0$ is the time when a substance (1,3,5-tri-tert-butylbenzene) that does not at all interact with the packing material is eluted). In addition, the separation factor α means a ratio of the retention factors of the both enantiomers. To be specific, it is calculated by the formula represented by: $α=k_2/k$ (wherein $k_1$ is the retention factor of the enantiomer which is eluted first, and $k_2$ is the retention factor of the enantiomer which is eluted later). Generally, when α is 1, it means that the elution time is completely the same and separation is not attainable. When α is >1, it means that the both enantiomers are separable. Generally, when α is 1.2 or above, it means that complete separation to the foot of the peak is attainable.

According to Table 1, it was confirmed that racemates of a wide variety of chiral compounds such as amide, ketone, phenol, alcohol, metal complex and the like can be separated extremely efficiently by using compound (I) or compound (I-h) of the present invention as the chiral stationary phase of HPLC column.

INDUSTRIAL APPLICABILITY

According to the present invention, optically active poly (diphenylacetylene) compound (compound (I)) and a compound having a main chain induced with a one-handed helical chirality (compound (I-h)) can be conveniently synthesized. Using the compound of the present invention, a wide variety of chiral compounds can be optically resolved, and separation ability is high. Therefore, a convenient and practical separation method of an optical isomer can be provided. Furthermore, since a commercially available compound can be widely used as an optically active chiral compound to be used for the production of compound (I), it is advantageous in that the kind thereof and absolute configuration thereof can be easily selected and optimized according to the kind of separation target compound and elution order.

The invention claimed is:

1. A poly(diphenylacetylene) compound represented by the formula (I):

[wherein
$R^1$, $R^{1'}$, $R^2$, $R^{2'}$, $R^3$, $R^{3'}$, $R^4$ and $R^{4'}$ are each independently a hydrogen atom, a halogen atom, an optionally substituted alkyl group, an optionally substituted cycloalkyl group, an optionally substituted alkoxy group, an optionally substituted alkylthio group, a tri-substituted silyl group, a tri-substituted siloxy group or an optionally substituted acyloxy group;
X is a carboxy group amidated or esterified by condensation with an optically active chiral compound; and
n is an integer of not less than 10],
or a salt thereof, or a solvate thereof.

2. The compound according to claim 1, which has a one-handed helical structure, or a salt thereof, or a solvate thereof.

3. The compound according to claim 1, wherein each of $R^1$ and $R^{1'}$, $R^2$ and $R^{2'}$, $R^3$ and $R^{3'}$, and $R^4$ and $R^{4'}$ are the same group, or a salt thereof, or a solvate thereof.

4. The compound according to claim 1, wherein X is a carboxy group amidated or esterified by condensation with an optically active form of a chiral compound selected from the group consisting of 1-phenylethylamine, 1-cyclohexylethylamine, 1-(1-naphthyl)ethylamine, 1-(2-naphthyl)ethylamine, sec-butylamine, 1-phenyl-2-(p-tolyl)ethylamine, 1-(p-tolyl)ethylamine, 1-(4-methoxyphenyl)ethylamine, β-methylphenethylamine, 2-amino-1-butanol, 2-amino-1,2-diphenylethanol, 1-amino-2-indanol, 2-amino-1-phenyl-1,3-propanediol, 2-amino-1-propanol, leucinol, phenylalaninol, 2-phenylglycinol, valinol, norephedrine, methioninol, 1-benzyl-3-aminopyrrolidine, 2-(methoxymethyl)pyrrolidine, 1-methyl-2-(1-piperidinomethyl)pyrrolidine, 1-(2-pyrrolidinomethyl)pyrrolidine, 1-phenylethylalcohol, 1-phenyl-2-propanol, 1,2,3,4-tetrahydro-1-naphthol, 1-acetyl-3-pyrrolidinol, 1-benzyl-3-pyrrolidinol, 2-butanol, α-hydroxy-γ-butyrolactone, 3-hydroxytetrahydrofuran, 1-methyl-3-pyrrolidinol, 2-octanol, 2-pentanol, 1-(2-naphthyl)ethanol, menthol, borneol, quinidine, quinine, quincorine, quincoridine, cinchonidine, cinchonine and an amino acid having a protected carboxy group, or a salt thereof, or a solvate thereof.

5. The compound according to claim 1, wherein $R^1$, $R^{1'}$, $R^2$, $R^{2'}$, $R^3$, $R^{3'}$, $R^4$ and $R^{4'}$ are each independently a hydrogen atom, a halogen atom, a $C_{1-6}$ alkyl group optionally substituted by halogen atom(s), a $C_{1-6}$ alkoxy group optionally substituted by halogen atom(s), a tri $C_{1-6}$ alkylsilyl group or a tri $C_{1-6}$ alkylsiloxy group, and each of $R^1$ and $R^{1'}$, $R^2$ and $R^{2'}$, $R^3$ and $R^{3'}$, and $R^4$ and $R^{4'}$ are the same group;
X is a carboxy group amidated by condensation with an optically active form of a compound selected from the group consisting of 1-phenylethylamine, 1-cyclohexylethylamine, 1-(1-naphthyl)ethylamine, 1-(2-naphthyl)ethylamine, sec-butylamine, 1-phenyl-2-(p-tolyl)ethylamine, 1-(p-tolyl)ethylamine, 1-(4-methoxyphenyl)ethylamine, β-methylphenethylamine, 2-amino-1-butanol, 2-amino-1,2-diphenylethanol, 1-amino-2-indanol, 2-amino-1-phenyl-1,3-propanediol, 2-amino-1-propanol, leucinol, phenylalaninol, 2-phenylglycinol, valinol, norephedrine, methioninol, 1-benzyl-3-aminopyrrolidine, 2-(methoxymethyl)pyrrolidine, 1-(2-pyrrolidinomethyl)pyrrolidine and an amino acid having a protected carboxy group; and
n is an integer of not less than 10 and not more than 10000, or a salt thereof, or a solvate thereof.

6. The compound according to claim 1, wherein $R^1$, $R^{1'}$, $R^2$, $R^{2'}$, $R^3$, $R^{3'}$, $R^4$ and $R^{4'}$ are each independently a hydrogen atom or a halogen atom, and each of $R^1$ and $R^{1'}$, $R^2$ and $R^{2'}$, $R^3$ and $R^{3'}$, and $R^4$ and $R^{4'}$ is the same group;
X is a carboxy group amidated by condensation with (S)-(−)-1-phenylethylamine or (R)-(+)-1-phenylethylamine; and
n is an integer of not less than 100 and not more than 10000, or a salt thereof, or a solvate thereof.

7. An optical isomer separating agent comprising the poly(diphenylacetylene) compound according to claim 1.

8. A packing material comprising the optical isomer separating agent according to claim 7 supported on a carrier.

9. A production method of the compound according to claim 2, or a salt thereof, or a solvate thereof, comprising a step of amidating or esterifying the carboxy group of the poly(diphenylacetylene) compound represented by the formula (II):

[wherein
$R^1$, $R^{1'}$, $R^2$, $R^{2'}$, $R^3$, $R^{3'}$, $R^4$ and $R^{4'}$ are each independently a hydrogen atom, a halogen atom, an optionally substituted alkyl group, an optionally substituted cycloalkyl group, an optionally substituted alkoxy group, an optionally substituted alkylthio group, a tri-substituted silyl group, a tri-substituted siloxy group or an optionally substituted acyloxy group; and n is an integer of not less than 10], by condensing with an optically active chiral compound, and a step of heat treating the aforementioned amidated or esterified compound.

10. The method according to claim 9, wherein the heat treatment is performed at about 90° C.

11. The method according to claim 9, wherein the optically active chiral compound is an optically active form of a compound selected from the group consisting of 1-phenylethylamine, 1-cyclohexylethylamine, 1-(1-naphthyl)ethylamine, 1-(2-naphthyl)ethylamine, sec-butylamine, 1-phenyl-2-(p-tolyl)ethylamine, 1-(p-tolyl)ethylamine, 1-(4-methoxyphenyl)ethylamine, β-methylphenethylamine, 2-amino-1-butanol, 2-amino-1,2-diphenylethanol, 1-amino-2-indanol, 2-amino-1-phenyl-1,3-propanediol, 2-amino-1-propanol, leucinol, phenylalaninol, 2-phenylglycinol, valinol, norephedrine, methioninol, 1-benzyl-3-aminopyrrolidine, 2-(methoxymethyl)pyrrolidine, 1-methyl-2-(1-piperidinomethyl)pyrrolidine, 1-(2-pyrrolidinomethyl)pyrrolidine, 1-phenylethylalcohol, 1-phenyl-2-propanol, 1,2,3,4-tetrahydro-1-naphthol, 1-acetyl-3-pyrrolidinol, 1-benzyl-3-pyrrolidinol, 2-butanol, α-hydroxy-γ-butyrolactone, 3-hydroxytetrahydrofuran, 1-methyl-3-pyrrolidinol, 2-octanol, 2-pentanol, 1-(2-naphthyl)ethanol, menthol, borneol, quinidine, quinine, quincorine, quincoridine, cinchonidine, cinchonine and an amino acid having a protected carboxy group.

12. The method according to claim 11, wherein the optically active chiral compound is (S)-(−)-1-phenylethylamine or (R)-(+)-1-phenylethylamine.

* * * * *